United States Patent [19]

Richard et al.

[11] Patent Number: 5,236,698
[45] Date of Patent: Aug. 17, 1993

[54] S-TRIAZINE DERIVATIVES CARRYING BENZALMALONATE SUBSTITUENTS, AND COSMETIC UV SCREENING COMPOSITIONS

[75] Inventors: Herve Richard; Madeleine Leduc, both of Paris; Alex Junino, Livry-Gargan, all of France

[73] Assignee: L'Oreal, Paris, France

[21] Appl. No.: 862,378

[22] Filed: Apr. 2, 1993

[30] Foreign Application Priority Data

Apr. 4, 1991 [FR] France .................. 91 04122

[51] Int. Cl.⁵ .................. A61K 7/42; A61K 7/48; A61K 9/12; C07D 251/00
[52] U.S. Cl. .................. 424/47; 8/405; 424/DIG. 1; 424/DIG. 5; 424/59; 424/60; 424/63; 424/70; 424/71; 424/72; 424/401; 514/844; 514/845; 514/846; 514/847; 514/938; 514/944; 544/196; 544/197
[58] Field of Search .................. 424/59, 60, 70, 47, 424/71; 544/197, 196, 198

[56] References Cited

U.S. PATENT DOCUMENTS

| | | | |
|---|---|---|---|
| 3,189,615 | 6/1965 | Heller et al. .................. | 424/60 |
| 3,211,729 | 10/1965 | Siegrist et al. .................. | 424/59 |
| 3,244,708 | 4/1966 | Duennenberger et al. .................. | 424/60 |
| 3,249,608 | 5/1966 | Biland et al. .................. | 424/59 X |
| 3,259,627 | 7/1966 | Duennenberger et al. .................. | 424/60 |
| 4,617,390 | 10/1986 | Hoppe et al. .................. | 424/59 UX |

FOREIGN PATENT DOCUMENTS

| | | | |
|---|---|---|---|
| 0087098 | 8/1983 | European Pat. Off. .................. | 424/59 |
| 935515 | 8/1963 | United Kingdom .................. | 544/197 |

OTHER PUBLICATIONS

"UV-Filte fur Haut-und Produktschutz in kosmetischen Formulierungen", Seifen et al., vol. 115, #18, Nov. 21, 1989, pp. 661-662.

*Primary Examiner*—Dale R. Ore
*Attorney, Agent, or Firm*—Jacobson, Price, Holman & Stern

[57] ABSTRACT

The invention relates to a compound of formula:

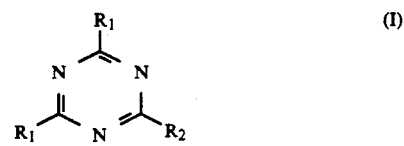

where $R_1$ is of the formula:

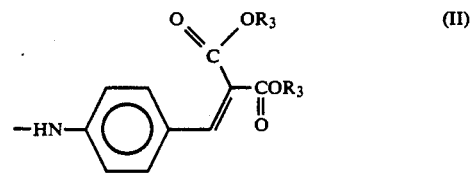

where $R_3$ represents a linear or branched $C_1$-$C_{20}$ alkyl; $R_2$ is identical to $R_1$ or is a halogen or a linear or branched $C_1$-$C_{20}$ alkoxy or mono- or dialkylamino or is of the formulae (III) or (IV):

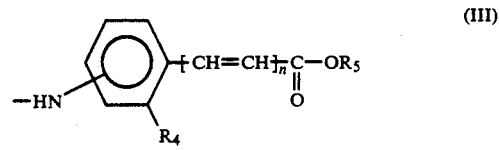

where $R_5$ is a linear or branched $C_1$-$C_{20}$ alkyl and n=0 or 1;
$R_4$ denotes H, OH or $C_1$-$C_5$ alkoxy;

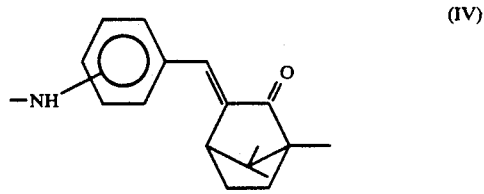

Application of these compounds to the protection of the skin and hair against ultraviolet radiation.

11 Claims, No Drawings

S-TRIAZINE DERIVATIVES CARRYING BENZALMALONATE SUBSTITUENTS, AND COSMETIC UV SCREENING COMPOSITIONS

The present invention relates to novel s-triazine derivatives carrying benzalmalonate substituents, a method for their preparation and their use as sunscreen agents, especially in the cosmetic field.

It is known that light radiation of wavelength between 280 nm and 400 nm permit tanning of the human epidermis and that rays of wavelengths between 280 and 320 nm, known under the name UV-B, cause erythemas and skin burns which can hamper the development of tanning; this UV-B radiation must therefore be screened out.

It is also known that UV-A rays of wavelengths between 320 and 400 nm, which bring about tanning of the skin, are capable of causing damage to it especially in the case of sensitive skin or skin continually exposed to solar radiation. UV-A rays cause in particular loss of elasticity of the skin and the appearance of wrinkles which lead to premature ageing. They promote the onset of erythemal reaction or amplify this reaction in some individuals and may even be responsible for phototoxic or photoallergic reactions.

It is therefore useful to have available compounds which are capable of absorbing both UV-A rays and UV-B rays which are harmful to the skin.

It is also desirable to provide the hair with good protection against photochemical damage in order to avoid, in particular, alteration of shade or bleaching.

It is known moreover that the constituents used in cosmetic preparations do not always possess adequate stability to light and deteriorate under the effect of light radiation.

Consequently, it is desirable to incorporate into these preparations compounds which are capable of screening out UV rays and which should possess in addition good stability and adequate solubility in the media normally used in cosmetics and, in particular, in oils and fats.

s-Triazine derivatives carrying p-aminobenzoate substituents are known from U.S. Pat. No. 4,617,390, which absorb only UV-B radiation and whose solubility in fatty substances is limited; it is therefore necessary, if it is desired to absorb the UV radiation as a whole, to combine UV-A screening agents with these s-triazine derivatives grafted through p-aminobenzoate residues.

The applicant company has discovered novel s-triazine derivatives grafted through residues which are capable of absorbing UV-A radiation or UV radiation as a whole (UV-B and UV-A) and which possess in addition excellent solubility in fatty substances. These s-triazine derivatives also possess a very high molar absorption coefficient which makes it possible to use them in low concentration, for example in cosmetic skin protection or antisun compositions. Combined with dibenzoylmethane type UV-A filters, especially 4-tert-butyl-4'-methoxydibenzoylmethane (Parsol 1789), they permit these compounds to be photostabilised.

In addition to their screening properties and their excellent fat-solubility, these novel s-triazine derivatives possess good chemical and photochemical stability and have the advantage of being neither toxic nor irritant and of being perfectly innocuous towards the skin.

The subject of the present invention is therefore novel compounds of the following formula (I):

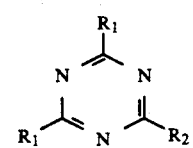

in which $R_1$ is of the formula:

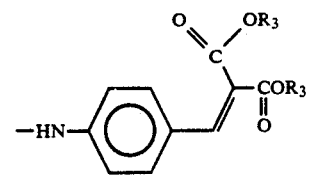

where $R_3$ represents a linear or branched alkyl radical containing 1 to 20 carbon atoms;

$R_2$ is identical to $R_1$, or is a halogen, a linear or branched alkoxy or mono- or dialkylamino group containing 1 to 20 carbon atoms or a group of the formulae (III) or (IV) below:

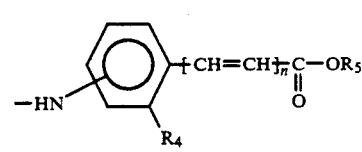

in which $R_5$ is a linear or branched alkyl radical containing 1 to 20 carbon atoms, and $n = 0$ or 1;

when n is equal to 0, $R_4$ represents a hydrogen atom, the amino residue being in position 4 with respect to the carboxyl group, or $R_4$ represents a hydroxyl radical or a $C_1$–$C_6$ alkoxy radical, the amino residue being in position 4 or 5 with respect to the carboxyl group;

when n is equal to 1, $R_4$ represents a hydrogen atom, the amino residue being in position 4 with respect to the unsaturated group,

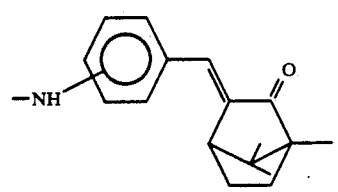

in which the amino residue is in position 2, 3 or 4 with respect to the methylidenecamphor group, provided that:

when $R_2 = R_1$, $R_3$ is a radical containing not less than 4 carbon atoms;

when $R_2 \neq R_1$ and is of the formula (III), $R_5$ contains not less than 4 carbon atoms when $R_3$ contains 1 to 7 carbon atoms;

when $R_2 \neq R_1$ and $R_2$ is not of the formula (III), but is an alkoxy or a mono- or dialkylamino radical, $R_2$ contains not less than 6 carbon atoms when $R_3$ contains 1 to 3 carbon atoms.

Among the linear or branched alkyl radicals, there may be mentioned for example: methyl, ethyl, n-propyl, isopropyl, n-butyl, isobutyl, tert-butyl, n-amyl, isoamyl, neopentyl, n-hexyl, n-heptyl, n-octyl, 2-ethylhexyl, n-dodecyl and n-octadecyl.

Among the alkoxy radicals, there may be mentioned methoxy, ethoxy, n-propoxy, isopropoxy, n-butoxy, isobutoxy, tert-butoxy, n-amyloxy, isoamyloxy, neopentyloxy, n-hexyloxy, n-heptyloxy, n-octyloxy, 2-ethylhexyloxy, n-dodecyloxy and n-octadecyloxy.

Among the halogens, there may be mentioned more particularly chlorine and bromine.

These novel compounds absorb UV-A radiation when $R_2$ is identical to $R_1$ or is a halogen, an alkoxy or mono- or dialkylamino group or is of the formula (IV) or (III) in which n is equal to 1, or n is equal to 0, and $R_4$ represents a hydroxyl radical, the amino residue being in position 5 with respect to the carboxyl group, or they absorb broad band UV radiation when $R_2$ is of the formula (III) in which n is equal to 0, and $R_4$ represents a hydrogen atom or a hydroxyl radical, the amino residue being in position 4 with respect to the carboxyl group, or a $C_1$-$C_6$ alkoxy radical, the amino residue being in position 4 or 5 with respect to the carboxyl group.

These novel s-triazine derivatives may be used as sunscreen agents for human skin and for the hair and as light-protecting agents in the plastics industry.

The subject of the present invention is also the method of preparing the compounds of formula (I).

The compounds of formula (I) may be obtained according to the reaction scheme below:

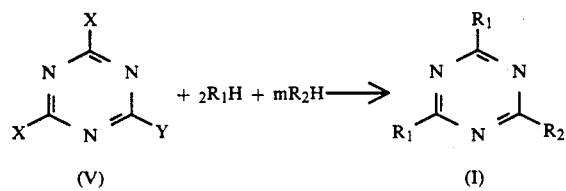

where $R_1$ is of the formula (II) which is given above, and $R_2$ has the same meaning as above; X represents a halogen, in particular chlorine or bromine, Y represents a halogen, in particular chlorine or bromine, or a linear or branched alkoxy or mono- or dialkylamino group containing 1 to 20 carbon atoms; m is an integer equal to 1 if $R_2$ is of the formula (II), (III) or (IV); in the other cases, m is equal to 0.

To obtain the compound (I) in which $R_2$ is identical to $R_1$ and is of the formula (II), a stoichiometric excess of the compound $R_1H$ of the order of 10% to 50% should be used relative to the compound (V) in which Y is a halogen.

Otherwise, a mixture of compound (I) in which $R_2$ is identical to $R_1$ and is of the formula (II), and of compound (I) in which $R_2$ is a halogen, is obtained. This mixture may be separated by conventional means such as chromatography, fractional crystallisation and the like.

The compounds of general formula (V) in which Y is different from X may be obtained according to the reaction scheme below, which is described in the publications: J. T. THURSTON et al., J. Am. Chem. Soc., 73, 2981 (1951) and J. R. DUDLEY et al., J. Am. Chem. Soc. 73, 2986 (1951):

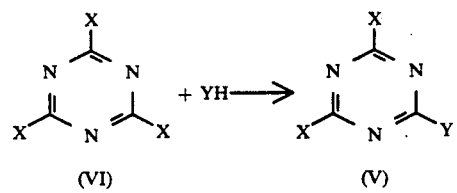

X and Y having the same meanings as above.

The above reactions may be carried out optionally in the presence of a solvent (for example: toluene, xylene or acetone/water), at a temperature between 0° and 250° C., more particularly between 0° and 150° C.

The compounds $R_1H$ and $R_2H$ where $R_2$ is of the formula (II) or (III) may be prepared according to known methods described in Patents FR-2,151,503, FR-A 2,385,685 and GB 1,064,116.

The compounds $R_2H$ where $R_2$ is of the formula (IV), that is to say the ortho-, meta- and para-aminobenzylidenecamphors, may be prepared in the following manner from the corresponding nitrobenzylidenecamphor derivatives.

Synthesis of ortho- and para-nitrobenzylidenecamphors

D,L-Benzylidenecamphor (200 g, 0.83 mol) in solution in 380 ml of 98% sulphuric acid is nitrated at 10° C. by dropwise addition of a mixture of 84.2 g of 65% nitric acid and 45 ml of 98% sulphuric acid. Stirring is maintained for 1 hour at 10°-20° C. after discontinuing the addition, and the reaction mixture is then poured into 4 litres of ice with vigorous stirring. The precipitate is washed with water and then recrystallised twice in isopropanol. 115 g (yield 48 %) of 4-nitrobenzylidenecamphor are obtained:
off-white powder
m.p. = 158° C.
UV: (95% ethanol) $\lambda_{max}$=314 nm ($\epsilon_{max}$=22800)
NMR spectrum conforms to the formula.

Ortho-nitrobenzylidenecamphor is isolated by concentration of the recrystallisation liquors at half-filtration of the precipitate and new recrystallisations in ethanol and then in diisopropyl ether:
light yellow powder
m.p. = 118° C.
UV: (95% ethanol) $\lambda_{max}$=256 nm ($\epsilon_{max}$=16350)
$\lambda_{max}$=320 nm (shoulder) ($\epsilon_{max}$=4390)
NMR spectra conform to the formula.

Synthesis of para-aminobenzylidenecamphor

A mixture of fine zinc powder (60 g), ethanol (250 ml), ammonium chloride (2 g) and water (20 ml) is heated to the reflux temperature and the paranitrobenzylidenecamphor (20 g, 0.07 mol) is added in portions with stirring. The mixture is allowed to reflux for half an hour, the zinc is filtered and the mixture is rinsed with alcohol. The filtrate is poured in ice (500 g). The precipitate obtained is filtered, washed with water and dried under vacuum. A quantitative yield of para-aminobenzylidenecamphor (17.7 g) is obtained. It is recrystallised in ethanol to give the expected derivative:
light yellow powder
m.p. = 144°-145° C.
UV: (95% ethanol) $\lambda_{max}$=357 nm ($\epsilon_{max}$=27500)
analysis: $C_{17}H_{21}NO$

|  | C % | H % | N % | O % |
| --- | --- | --- | --- | --- |
| Calculated: | 79.96 | 8.29 | 5.49 | 6.27 |
| Found: | 79.94 | 8.31 | 5.53 | 6.42 |

Synthesis of ortho-aminobenzylidenecamphor

The ortho-aminobenzylidenecamphor derivative is obtained in the same manner as above starting from ortho-nitrobenzylidenecamphor:
lemon yellow powder
m.p. = 155° C.
UV: (95% ethanol) $\lambda_{max}$=290 nm ($\epsilon_{max}$=9880) $\lambda_{max}$=366 nm ($\epsilon_{max}$=5870)
NMR spectra conform to the formula.

Synthesis of meta-nitrobenzylidenecamphor

The camphor (50.2 g, 0.33 mol), dimethoxyethane (180 ml) and sodium hydride (32 g at 50% in oil, 0.33 mol) washed with dimethoxyethane, are placed in a round-bottom flask. The mixture is heated under nitrogen to 80° C. and the meta-nitrobenzaldehyde (45.3 g, 0.3 mol) dissolved in dimethoxyethane (100 ml) is added dropwise over half an hour. The mixture is left stirring at 80° C. for 1.5 hours. The reaction mixture is allowed to cool and it is poured cautiously in 2 litres of acidified and ice cold water. The brown precipitate obtained is filtered, washed with water and dried. After recrystallisation in diisopropyl ether in the presence of vegetable black, 20 g of meta-nitrobenzylidenecamphor are obtained.
Light beige powder
m.p = 113° C.
NMR spectrum conforms to the formula.

Synthesis of meta-aminobenzylidenecamphor

The reduction of the meta-nitrobenzylidenecamphor is carried out in the same manner as that of the above ortho- and para-nitrobenzylidenecamphors. Metaaminobenzylidenecamphor is obtained after recrystallisation in diisopropyl ether:
light yellow powder
m.p. = 77°–78° C.
UV: (95% ethanol) $\lambda_{max}$=295 nm ($\epsilon_{max}$=18950)
analysis: $C_{17}H_{21}NO$

|  | C % | H % | N % | O % |
| --- | --- | --- | --- | --- |
| Calculated: | 79.96 | 8.29 | 5.49 | 6.27 |
| Found: | 79.81 | 8.36 | 5.49 | 6.48 | p-Aminobenzylidenecamphor, which is a known compound, may also be prepared as described by HALLER, BOUDIN, Annales de Chimie, 9th series, volume XVII (1922).

Among the compounds of formula (I) above, there may be mentioned more particularly:

1) . 2,4,6-tris(diisobutyl 4'-aminobenzalmalonate)-s-triazine
2) . 2,4-bis[di(2-ethylhexyl) 4'-aminobenzalmalonate]-6-chloro-s-triazine
3) . 2,4,6-tris[di(2-ethylhexyl) 4'-aminobenzalmalonate]-s-triazine
4) . 2,4-bis[di(2-ethylhexyl) 4'-aminobenzalmalonate]-6-(2-ethylhexyl 4'-aminobenzoate)-s-triazine
5) . 2,4-bis(diisobutyl 4'-aminobenzalmalonate)-6-butoxy-s-triazine
6) . 2,4-bis(diisobutyl 4'-aminobenzalmalonate)-6-(2-ethylhexylamino)-s-triazine
7) . 2,4-bis(diisobutyl 4 -aminobenzalmalonate)-6-(2-ethylhexyl 5'-aminosalicylate)-s-triazine
8) . 2,4-bis(diisobutyl 4'-aminobenzalmalonate)-6-(2-ethylhexyl 4'-aminocinnamate)-s-triazine
9) . 2,4-bis(diisobutyl 4,-aminobenzalmalonate)-6-(4'-aminobenzylidenecamphor)-s-triazine.

By virtue of their fat solubility, the compounds of formula (I) above become uniformly distributed inside conventional cosmetic carriers containing at least one cosmetically acceptable fatty phase or organic solvent, and may be applied to the skin or the hair to form an effective protective film.

The subject of the present invention is therefore also a cosmetic composition containing, in a cosmetically acceptable carrier containing at least one fatty phase or one organic solvent, an effective amount of at least one compound of formula (I) above.

The cosmetic composition of the invention may also be used as human epidermis- or hair-protecting composition or as antisun composition.

The subject of the present invention is also a method of protecting the skin and natural hair or hair sensitized to solar radiation, which consists in applying to the skin or the hair, an effective amount of a cosmetic composition containing at least one compound of formula (I).

"Sensitized hair" is understood to mean hair which has undergone permanent wave, dyeing or bleaching treatment.

The subject of the invention is also a coloured or colourless cosmetic composition, stabilised with respect to light, containing an effective amount of at least one compound of formula (I) above.

When it is used as a composition intended for protecting the human epidermis against ultraviolet rays, the cosmetic composition according to the invention may be provided in the most diverse forms normally used for this type of composition. It may in particular be provided in the form of oily or oil-alcohol lotions, emulsions such as a cream or a milk, vesicular dispersions of ionic or nonionic amphiphilic lipids, oil-alcohol or alcoholic gels, solid sticks or they may be packaged as an aerosol. The creams constitute what is generally called "protective day creams" for daily use.

It may contain the cosmetic adjuvants normally used in this type of composition, such as thickeners, demulcents, humectants, surface-active agents, preservatives, antifoams, perfumes, oils, waxes, lanolin, propellants, colorants and/or pigments whose role is to colour the composition itself or the skin, or any other ingredient normally used in cosmetics.

It may in addition contain other UV-A and/or UV-B screens.

The compound of formula (I) is present in proportions between 0.1 and 2% relative to the total weight of the cosmetic human epidermis-protecting composition.

An oil, a wax and generally any fatty substance, a lower monoalcohol or polyol or mixtures thereof, may be used as solubilising solvent. The monoalcohols or polyols more particularly preferred are ethanol, isopropanol, propylene glycol, hexylene glycol, glycerin and sorbitol.

One embodiment of the invention is an emulsion in the form of a protective cream or oil containing, in addition to the compound of formula (I), fatty alcohols, fatty acid esters and in particular fatty acid triglycerides, fatty acids, lanolin, natural or synthetic oils or waxes and emulsifiers, in the presence of water.

The vesicular dispersions of ionic or nonionic amphiphilic lipids may be prepared according to known methods.

The lipids may for example be swollen in an aqueous solution to form spherules dispersed in the aqueous medium as described in the article BANGHAN, STANDISH & WATKINS, J. Mol. Biol., 13,238 (1965) or in Patents FR-2,315,991 and 2,416,008 by the applicant company.

Another embodiment consists of oily lotions based on natural or synthetic oils and waxes, lanolin, fatty acid esters, in particular fatty acid triglycerides, or of oil-alcohol lotions based on a lower alcohol such as ethanol or a glycol such as propylene glycol and/or a polyol such as glycerin and oils, waxes and fatty acid esters such as fatty acid triglycerides.

The cosmetic composition of the invention may also be an alcoholic gel containing one or more lower alcohols or polyols such as ethanol, propylene glycol or glycerin and a thickener such as silica. The oil-alcohol gels in addition contain a natural or synthetic oil or wax.

The solid sticks consist of natural or synthetic waxes and oils, fatty alcohols, fatty acid esters, lanolin and other fatty substances.

Conventional propellants are used in the case of a composition packaged as an aerosol.

The present invention also relates to cosmetic antisun compositions containing at least one compound of formula (I) and which may contain other UV-B and/or UV-A screening agent.

In this case, the total amount of screening agents present in the antisun composition, that is to say the compound of formula (I) and, optionally, the other screening agents, is between 0.3 and 15% by weight relative to the total weight of the antisun composition.

These antisun compositions are provided in the forms indicated above for the human epidermis-protecting compositions.

As sunscreen agents screening out UV-B rays, there may be mentioned water-soluble screening agents such as the benzylidenecamphor derivatives described in French Patents 2,199,971; 2,236,515; 2,282,426 and 2,383,904, by the applicant company, and more particularly 4-(2-oxo-3-bornylidenemethyl)phenyl-trimethylammonium methyl sulphate, and the salts of 4-(2-oxo-3-bornylidenemethyl)benzenesulphonic acid, 2-methyl-5-(2-oxo-3-bornylidenemethyl)benzenesulphonic acid, 3-benzylidene-2-oxo-10-bornanesulphonic acid and 2-phenylbenzimidazole-5-sulphonic acid.

The compounds according to the invention may also be combined with UV-B screening agents consisting of fatsoluble compounds or of oils having screening properties, such as in particular coffee oil. As fat-soluble UV-B sunscreen agents, there may be mentioned salicylic acid derivatives such as 2-ethylhexyl salicylate or homomethyl salicylate, cinnamic acid derivatives such as 2-ethylhexyl p-methoxycinnamate or 2-ethoxyethyl p-methoxycinnamate, p-aminobenzoic acid derivatives such as amyl p-aminobenzoate or 2-ethylhexyl p-dimethylaminobenzoate, benzophenone derivatives such as 2-hydroxy-4-methoxybenzophenone or 2,2'-dihydroxy-4-methoxybenzophenone, camphor derivatives such as 3-(4'-methylbenzylidene)camphor or 3-benzylidenecamphor.

The compounds according to the invention may also be combined with UV-A screening agents among which there may be mentioned dibenzoylmethane derivatives, for example 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane, as well as 1,4-benzene[di(3-methylidenecamphor)] derivatives sulphonated on the methyl radical in position 10 of the camphor such as described in French Patents 2,528,420 and 2,639,347.

It is understood that the abovementioned list of sunscreen agents used in combination with the compounds (I) according to the invention is not limiting.

When the cosmetic composition according to the invention is intended for protecting natural or sensitized hair from UV rays, this composition may be provided in the form of a shampoo, lotion, rinse off gel or emulsion to be applied before or after shampooing, before or after dyeing or bleaching, or before or after permanent waving, hair styling or treating lotion or gel, blow drying or hair setting lotion or gel, hair lacquer, composition for permanent waving, dyeing or bleaching of hair. This composition may contain, in addition to the compound of the invention, various adjuvants used in this type of composition, such as surface-active agents, thickeners, polymers, demulcents, preservatives, foam stabilisers, electrolytes, organic solvents, silicone derivatives, oils, waxes, anti-fat agents, colorants and/or pigments whose role is to colour the composition itself or the hair, or any other ingredient normally used in hair care.

It contains 0.1 to 2% by weight of the compound of formula (I).

The present invention also relates to cosmetic compositions containing at least one compound of formula (I) as protective agent against ultraviolet rays, consisting of hair compositions such as hair lacquers, hair setting lotions, optionally, for treating or disentangling, dyeing shampoos, hair dyeing compositions; make-up products such as nail varnishes, epidermal treatment creams and oils, foundations, lipsticks, skin care compositions such as bath oils or creams, as well as any other cosmetic composition which may present problems of stability to light during storage because of its constituents.

Such compositions contain 0.1 to 2% by weight of the compound of formula (I).

The compounds (I) according to the invention may also be incorporated into various organic materials, and in particular plastics, for the purpose of protecting them against ultraviolet radiation.

The invention will be better illustrated, without however being limited, by the following exemplary embodiments.

EXAMPLE 1

2,4,6-Tris(diisobutyl 4'-aminobenzalmalonate)-s-triazine

Cyanuric chloride (5.28 g, 0.0286 mol) and diisobutyl 4-aminobenzalmalonate (33.5 g, 0.105 mol) are refluxed for 10 hours, under nitrogen, in xylene (135 ml). The reaction mixture is concentrated under vacuum, passed through a silica column (eluent: $CH_2Cl_2$) and recrystallised from methanol to give the derivative of Example 1 (20.6 g; yield=68%):
light yellow powder m.p.=97° C.
UV: (95% ethanol) $\lambda_{max}$=355 nm ($\epsilon_{max}$=119600)
analysis: $C_{57}H_{72}N_6O_{12}$

|  | C % | H % | N % | O % |
| --- | --- | --- | --- | --- |
| Calculated: | 66.26 | 7.02 | 8.13 | 18.58 |
| Found: | 66.17 | 7.04 | 8.10 | 18.47 |

EXAMPLES 2 and 3

2,4-Bis[di(2-ethylhexyl) 4'-aminobenzalmalonate[-6-chloro-s-triazine and 2,4,6-tris[di(2-ethylhexyl)4'-aminobenzalmalonate]-s-triazine Cyanuric chloride (4.88 g, 0.027 mol) and di(2-ethylhexyl) 4-aminobenzalmalonate (35.2 g, 0.082 mol) are refluxed for 10 hours, under nitrogen, in xylene (130 ml). The mixture is cooled and the solvent is evaporated under vacuum. The oil obtained is chromatographed on a silica column (eluent: $CH_2Cl_2$). 2.2 g of the derivative of Example 2 having the following characteristics, are obtained from the first fractions:
light yellow powder
m.p.=70° C.
UV: (95% ethanol) $\lambda_{max}$=345 nm ($\epsilon_{max}$=58100)
$\lambda_{max}$=326 nm ($\epsilon_{max}$=57700)
analysis: $C_{55}H_{80}ClN_5O_8$

|  | C % | H % | Cl % | N % | O % |
| --- | --- | --- | --- | --- | --- |
| Calculated: | 67.77 | 8.27 | 3.64 | 7.18 | 13.13 |
| Found: | 67.80 | 8.30 | 3.76 | 7.20 | 13.34 |

20.8 g of the derivative of Example 3 having the following characteristics, are obtained in the subsequent fractions:
yellow wax
UV=(95% ethanol) $\lambda_{max}$=355 nm ($\epsilon_{max}$=108000)
analysis: $C_{81}H_{120}N_6O_{12}$

|  | C % | H % | N % | O % |
| --- | --- | --- | --- | --- |
| Calculated: | 71.02 | 8.83 | 6.13 | 14.02 |
| Found: | 71.18 | 8.81 | 6.21 | 13.88 |

EXAMPLE 4

2,4-Bis[di(2'-ethylhexyl) 4'-aminobenzalmalonate]-6-2-ethylhexyl 4'-aminobenzoate)-s-triazine The derivative of Example 2 (0.97 g, $10^{-3}$ mol) is refluxed in xylene (1.6 ml), under nitrogen, for 6 hours, with 2-ethylhexyl 4-aminobenzoate (0.25 g, $10^{-3}$ mol). After cooling, the solvent is evaporated under vacuum and the oil obtained is chromatographed on silica to give 0.95 g of the derivative of Example 4 having the following characteristics:
yellow wax
UV: (ethanol at 95°) $\lambda_{max}$=340 nm ($\epsilon_{max}$=79400)
$\lambda_{max}$=300 nm (shoulder) ($\epsilon_{max}$=43300)
analysis: $C_{70}H_{102}N_6O_{10}$

|  | C % | H % | N % | O % |
| --- | --- | --- | --- | --- |
| Calculated: | 70.79 | 8.66 | 7.08 | 13.47 |

| -continued | | | | |
| --- | --- | --- | --- | --- |
|  | C % | H % | N % | O % |
| Found: | 70.83 | 8.72 | 7.17 | 13.71 |

EXAMPLE 5

2,4-Bis(diisobutyl 4'-aminobenzalmalonate)-6-butoxy-s-triazine

2-Butoxy-4,6-dichloro-s-triazine (11.1 g, 0.05 mol) and diisobutyl 4-aminobenzalmalonate (35.13 g, 0.11 mol) are refluxed for 3 hours in toluene (350 ml). After cooling, a saturated solution of sodium bicarbonate is added to neutralise the mixture and the organic phase is washed with water and dried over sodium sulphate. After removing the solvent, the residue obtained is chromatographed on a silica column (eluent: $CH_2Cl_2$) to give 4 g of the derivative of Example 5 having the following characteristics:
powder with a shimmer of yellow
m.p.=104°-110° C.
UV: (95% ethanol) $\lambda_{max}$=348 nm ($\epsilon_{max}$=62000)
analysis: $C_{43}H_{57}N_5O_9$

|  | C % | H % | N % | O % |
| --- | --- | --- | --- | --- |
| Calculated: | 65.55 | 7.29 | 8.89 | 18.27 |
| Found: | 65.15 | 7.27 | 8.79 | 18.56 |

EXAMPLE 6

2,4-Bis(diisobutyl 4'-aminobenzalmalonate)-6-(2-ethylhexylamino)-s-triazine

A solution of cyanuric chloride (0.2 mol, 36.8 g) in acetone (300 ml) is introduced dropwise into crushed ice (100 g) in a round-bottom flask, with vigorous stirring, followed by a solution of 2-ethylhexylamine in acetone (100 ml), while maintaining the temperature between 0° and 5° C., and finally a solution of sodium carbonate (11.2 g, 0.1 mol) in 300 ml of water. The mixture is left stirring for one hour at 0°-5° C. The oil is extracted with dichloromethane, the organic phase is washed with water and dried over sodium sulphate. After evaporation of the solvent, 2-(2-ethylhexylamino)-4,6-dichloro-s-triazine (52 g, yield=95%) having the following characteristics, is obtained:
white powder
m.p.=37° C.
analysis: $C_{11}H_{18}Cl_2N_4$

|  | C % | H % | Cl % | O % |
| --- | --- | --- | --- | --- |
| Calculated: | 47.66 | 6.55 | 25.58 | 20.21 |
| Found: | 47.89 | 6.60 | 25.79 | 20.16 |

The above derivative (13.8 g, 0.05 mol) is refluxed in xylene (230 ml), under nitrogen, for 8 hours, with diisobutyl 4-aminobenzalmalonate (35.13 g, 0.11 mol). After cooling, the mixture is poured into ice cold water and neutralised with a saturated solution of sodium carbonate. It is extracted with dichloromethane and the organic phase is washed twice with water. A brown gum is obtained which is chromatographed on silica to give 23 g of the derivative of Example 6 having the following characteristics:

pale yellow amorphous powder
UV: (95% ethanol) $\lambda_{max}=354$ nm ($\epsilon_{max}=70550$)
analysis: $C_{47}H_{66}N_6O_8$

|  | C % | H % | N % | O % |
|---|---|---|---|---|
| Calculated: | 66.96 | 7.89 | 9.97 | 15.18 |
| Found: | 66.86 | 7.87 | 9.94 | 15.20 |

EXAMPLE 7

2,4-Bis(diisobutyl 4'-aminobenzalmalonate)-6-(2-ethylhexyl 5'-aminosalicylate)-s-triazine Cyanuric chloride (0.05 mol, 9.22 g) in acetone (50 ml) is placed in a round-bottom flask. The solution is cooled to 5°-10° C., 50 ml of water are added followed, dropwise, by 2-ethylhexyl 5-aminosalicylate (0.05 mol, 13.26 g) in 50 ml of acetone. Sodium bicarbonate (0.05 mol, 4.2 g) in solution in 100 ml of water is then added and the mixture is left stirring for two hours. The precipitate obtained is drained and recrystallised from ethanol to give 2-(2-ethylhexyl 5'-aminosalicylate)-4,6-dichloro-s-triazine (17 g, yield=83%) having the following characteristics:
white powder
m.p.=131° C.
analysis: $C_{18}H_{22}Cl_2N_4O_3$

|  | C % | H % | Cl % | N % | O % |
|---|---|---|---|---|---|
| Calculated: | 52.31 | 5.37 | 17.16 | 13.56 | 11.61 |
| Found: | 52.50 | 5.39 | 17.08 | 13.48 | 11.83 |

The above derivative (4.13 g, 0.01 mol) is refluxed in xylene (47 ml), under nitrogen, for 10 hours, with diisobutyl 4-aminobenzalmalonate (6.7 g, 0.021 mol). After cooling, the mixture is poured into ice cold water and neutralised with a solution of sodium bicarbonate. The organic phase is washed twice with water and dried over sodium sulphate. After removing the solvent, the oil obtained is chromatographed on silica (eluent: $CH_2Cl_2$) to give the compound of Example 7 having the following characteristics:
light yellow amorphous powder
UV: (95% ethanol) $\lambda_{max}=355$ nm ($\epsilon_{max}=82120$)
analysis: $C_{54}H_{70}N_6O_{11}$

|  | C % | H % | N % | O % |
|---|---|---|---|---|
| Calculated: | 66.24 | 7.21 | 8.58 | 17.97 |
| Found: | 66.25 | 7.25 | 8.39 | 17.89 |

EXAMPLE 8

2,4-Bis(diisobutyl 4'-aminobenzalmalonate)-6-(2-ethylhexyl 4'-aminocinnamate)-s-triazine Cyanuric chloride (0.01 mol, 1.85 g) in acetone (10 ml) is placed in a round-bottom flask. The solution is cooled to 5°-10° C. 5 ml of water are added followed, dropwise, by 2-ethylhexyl 4-aminocinnamate (0.01 mol, 2.75 g) in 50 ml of acetone. Sodium bicarbonate (0.01 mol, 0.84 g) in solution in 50 ml of water is then added and the mixture is left stirring for half and hour. The precipitate obtained is drained and dried to give 2-(2-ethylhexyl 4'-aminocinnamate)-4,6-dichloro-s-triazine (4 g, yield=94%) having the following characteristics:
light yellow powder
m.p.=140° C.
analysis: $C_{20}H_{24}Cl_2N_4O_2$

|  | C % | H % | Cl % | N % | O % |
|---|---|---|---|---|---|
| Calculated: | 56.74 | 5.71 | 16.75 | 13.23 | 7.56 |
| Found: | 56.78 | 5.80 | 16.89 | 13.10 | 7.80 |

The above derivative (3.17 g, 7.5 $10^{-3}$ mol) is refluxed in xylene (35 ml), under nitrogen, for 7 hours, with diisobutyl 4-aminobenzalmalonate (5.27 g, 0.016 mol). After cooling, the mixture is neutralised with a saturated solution of sodium carbonate. The organic phase is washed twice with water and dried over sodium sulphate. After removing the solvent, the oil obtained is chromatographed on silica (eluent: $CH_2Cl_2$) to give the compound of Example 8 (5.2 g, yield=70 %) having the following characteristics:
light yellow amorphous powder
UV: (95% ethanol) $\lambda_{max}=354$ nm ($\epsilon_{max}=113000$)
analysis: $C_{56}H_{72}N_6O_{10}$

|  | C % | H % | N % | O % |
|---|---|---|---|---|
| Calculated: | 67.99 | 7.34 | 8.50 | 16.17 |
| Found: | 67.62 | 7.52 | 8.36 | 16.51 |

EXAMPLE 9

4-Bis(diisobutyl 4'-aminobenzalmalonate)-6-4'-aminobenzylidenecamphor)-s-triazine Cyanuric chloride (0.05 mol, 9.2 g) in acetone (100 ml) is placed in a round-bottom flask. The solution is cooled to 5°-10° C., 50 ml of water are added followed, dropwise, around 0°-5° C., by 4-aminobenzylidenecamphor (0.05 mol, 12.7 g) in 100 ml of acetone. Sodium bicarbonate (0.05 mol, 4.2 g) in solution in 50 ml of water is then added and the mixture is left stirring for half an hour. The precipitate obtained is drained and dried to give 2-(4'-aminobenzylidenecamphor)-4,6-dichloro-s-triazine (19.5 g, yield=97%) having the following characteristics:
light yellow powder
m.p.=250° C.
analysis: $C_{20}H_{20}Cl_2N_4O$

|  | C % | H % | Cl % | N % | O % |
|---|---|---|---|---|---|
| Calculated: | 59.56 | 5.00 | 13.89 | 3.97 | 17.58 |
| Found: | 59.76 | 5.01 | 13.76 | 4.15 | 17.53 |

The above derivative (8.06 g, 0.02 mol) is refluxed in xylene (95 ml), under nitrogen, for 6 hours, with diisobutyl 4-aminobenzalmalonate (14.05 g, 0.044 mol). After cooling, the mixture is neutralised with a saturated solution of sodium bicarbonate. The organic phase is washed twice with water and dried over sodium sulphate. After removing the solvent, the gum obtained is chromatographed on silica (eluent: $CH_2Cl_2$) to give the derivative of Example 9 (13.3 g, yield=69%) having the following characteristics:
light yellow amorphous powder
UV: (95% ethanol) $\lambda_{max}=356$ nm ($\epsilon_{max}=108500$)

analysis: $C_{56}H_{68}N_6O_9$

|  | C % | H % | N % | O % |
|---|---|---|---|---|
| Calculated: | 69.40 | 7.07 | 8.67 | 14.66 |
| Found: | 68.80 | 7.11 | 8.41 | 15.24 |

EXAMPLES OF FORMULATION

Example A

| Antisun cream | |
|---|---|
| Phase A | |
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Oxypropylenated myristyl alcohol containing 3 mol of propylene oxide sold under the name "WITCONOL APM" by WITCO | 15.0 g |
| 2,4-Bis(diisobutyl 4'-aminobenzalmalonate)-6-butoxy-s-triazine (Example 5) | 3.0 g |
| 2-Ethylhexyl p-dimethylaminobenzoate | 4.0 g |
| Phase B | |
| Glycerin | 20.0 g |
| Water qs | 100.0 g |
| Phase C | |
| Perfume, preservatives for the two phases A and B qs | |

PROCEDURE

The phases A and B are heated in a water bath at 80° C.
The phase A is poured into the phase B with vigorous stirring for 5 minutes.
The stirring is continued up to 40° C.
The perfume and the preservatives are then added at around 40° C.
The mixture is stirred to room temperature.

Example B

| Antisun cream | |
|---|---|
| Phase A | 7.0 g |
| Mixture of cetylstearyl alcohol and oxyethylenated cetylstearyl alcohol containing 33 mol of ethylene oxide sold under the name "SINNOWAX AO" by HENKEL | |
| Mixture of glycerol mono- and distearate, non-self-emulsifying | 2.0 g |
| Cetyl alcohol | 1.5 g |
| Silicon oil | 1.5 g |
| Oxypropylenated myristyl alcohol containing 3 mol of propylene oxide sold under the name "WITCONOL APM" by WITCO | 15.0 g |
| 2,4,6-Tris[di(2-ethylhexyl) 4'-aminobenzalmalonate]-s-triazine (Example 3) | 5.0 g |
| Phase B | |
| Triethanolamine salt of 2-phenylbenzimidazole-5-sulphonic acid | 3.0 g |
| Glycerin | 20.0 g |
| Water qs | 100.0 g |
| Phase C | |
| Perfume, preservatives for the two phases A and B qs | |

The procedure is the same as in Example A.

Example C

| Human epidermis-protecting cream | |
|---|---|
| Phase A | |
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Oxypropylenated myristyl alcohol containing 3 mol of propylene oxide sold under the name "WITCONOL APM" by WITCO | 15.0 g |
| 2,4-Bis(diisobutyl 4'-aminobenzalmalonate)-6-(4'-aminobenzylidenecamphor)-s-triazine (Example 9) | 1.0 g |
| Phase B | |
| Glycerin | 20.0 g |
| Water qs | 100.0 g |
| Phase C | |
| Perfume, preservatives for the two phases A and B qs | |

The procedure is the same as in Example A.

Example D

| Human epidermis-protecting (oil-in-water) cream | |
|---|---|
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Capric/caprylic acid triglycerides sold under the tradename of "MIGLYOL 812" by DYNAMIT NOBEL | 20.0 g |
| 2,4,6-Tris(diisobutyl 4'-aminobenzalmalonate)-s-triazine (Example 1) | 1.0 g |
| 4-Tert-butyl-4'-methoxybenzoylmethane sold under the tradename of "PARSOL 1789" by GIVAUDAN | 1.0 g |
| Glycerin | 20.0 g |
| Perfume, preservatives qs | |
| Water qs | 100.0 g |

The oily phase containing the emulsifiers and the screening agents is heated to 80° C.
The aqueous phase containing glycerin is heated to the same temperature. The oily phase is then poured into the aqueous phase with vigorous stirring. The stirring is continued while allowing the mixture to cool. The perfume and preservatives are added at around 40° C.

Example E

| Antisun oil | |
|---|---|
| The following ingredients are mixed while optionally heating to 40-45° C. to homogenise: | |
| Liquid paraffin | 2.5 g |
| 2,4,6-Tris(diisobutyl 4'-aminobenzalmalonate)-s-triazine (Example 1) | 2.0 g |
| Di-tert-butylhydroxytoluene | 0.05 g |
| Perfume qs | |
| $C_8$-$C_{12}$ fatty acid triglycerides sold under the name "MIGLYOL 812" by DYNAMIT NOBEL | 40 g |
| 2-Ethylhexyl p-methoxycinnamate | 2 g |

-continued

| Antisun oil | |
|---|---|
| The following ingredients are mixed while optionally heating to 40–45° C. to homogenise: | |
| Alcohol, 96° qs | 100 g |

Example F

| Antisun oil | |
|---|---|
| The following ingredients are mixed while optionally heating to 40–45° C. to homogenise: | |
| 2,4-Bis[di(2-ethylhexyl) 4'-aminobenzal-malonate]-6-(2-ethylhexyl 4'-aminobenzoate)-s-triazine (Example 4) | 3.0 g |
| Alcohol, 96° | 15 g |
| Perfume qs | |
| Propylene glycol | 10 g |
| Diisopropyl adipate sold under the tradename of "CERAPHYL 230" by Van DYK qs | 100 g |

Example G

| Antisun oil | |
|---|---|
| The following ingredients are mixed while optionally heating to 40–45° C. to homogenise: | |
| 2,4-Bis[di(2-ethylhexyl) 4'-aminobenzal-malonate]-6-(2-ethylhexyl 4'-aminobenzoate)-s-triazine (Example 4) | 2.0 g |
| $C_{12}$–$C_{15}$ fatty alcohol benzolate sold under the name of "FINSOLV TN" by FINETEX | 30 g |
| Sunflower oil | 20 g |
| Perfume qs | |
| Cyclic dimethylpolysiloxane sold under the name "VOLATILE SILICONE 7207" by UNION CARBIDE qs | 100 g |

Example H

| Human epidermis-protecting oil-in-water emulsion | |
|---|---|
| 2,4-Bis[di(2-ethylhexyl) 4'-aminobenzal-malonate]-6-(2-ethylhexyl 4'-aminobenzoate)-s-triazine (compound of Example 4) | 2.0 g |
| Triethanolamine salt of 1,4-benzene-[di(3-methylidenecamphomethylsulphonic)] acid | 2.0 g |
| Mixture of cetylstearyl alcohol and oxyethylenated cetylstearyl alcohol containing 33 mol of ethylene oxide ("SINNOWAX AO" sold by HENKEL) | 7.0 g |
| Glycerol monostearate | 2.0 g |
| Propylene glycol | 10.0 g |
| Cetyl alcohol | 1.5 g |
| $C_{12}$–$C_{15}$ alcohol benzoate ("FINSOLV TN" sold by WITCO) | 15.0 g |
| Preservative | 0.2 g |
| Perfume qs | |
| Deionised water qs | 100 g |

The emulsion is prepared in the following manner:
The fatty substances and the emulsifiers are heated to around 70°–75° C.; the compound of Example 4 is added. On the other hand, water containing disulphonic acid neutralised with triethanolamine is heated to 70°–75° C. and the fatty phase is added to the aqueous phase. After stirring vigorously for 10 minutes, the mixture is allowed to cool while stirring gently, and the preservative and perfume are added at around 40° C.

EXAMPLE I

| Hair-protecting oil | |
|---|---|
| 2,4,6-Tris[di(2-ethylhexyl) 4'-aminobenzalmalonate]-s-triazine (compound of Example 3) | 1.0 g |
| Oleyl alcohol | 19.5 g |
| Hexylene glycol | 0.5 g |
| Colza oil qs | 100 g |

This oil, of opalescent appearance, is applied to dry hair, to which it gives sheen and softness while preserving its colour when it is exposed to natural light.

Example J

| Protective day cream | |
|---|---|
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Capric/caprylic acid triglycerides sold under the tradename of "MIGLYOL 812" by DYNAMIT NOBEL | 20.0 g |
| 2,4,6-Tris(diisobutyl 4'-aminobenzal-malonate)-s-triazine (Example 1) | 1.0 g |
| 4-Tert-butyl-4'-methoxybenzoylmethane sold under the tradename of "PARSOL 1789" by GIVAUDAN | 1.0 g |
| Glycerin | 20.0 g |
| Perfume, preservatives qs | |
| Water qs | 100.0 g |

We claim:
1. A compound of formula:

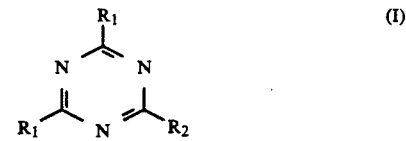 (I)

in which $R_1$ is of the formula:

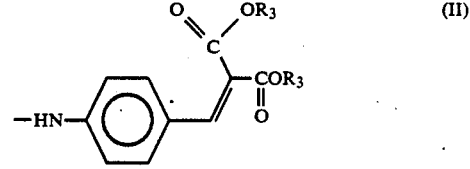 (II)

where $R_3$ represents a linear or branched alkyl radical containing 1 to 20 carbon atoms;

$R_2$ is identical to $R_1$, or is a halogen, a linear or branched alkoxy or mono- or dialkylamino group containing 1 to 20 carbon atoms or a group of the formulae (III) or (IV) below:

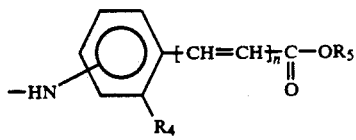 (III)

in which $R_5$ is a linear or branched alkyl radical containing 1 to 20 carbon atoms, and n=0 or 1; when n is equal to 0, $R_4$ represents a hydrogen atom, the amino group being in position 4 with respect to the carboxyl group, or $R_4$ represents a hydroxyl radical or a $C_1-C_6$ alkoxy radical, the amino group being in position 4 or 5 with respect to the carboxyl group;

when n is equal to 1, $R_4$ represents a hydrogen atom, the amino group being in position 4 with respect to the unsaturated group,

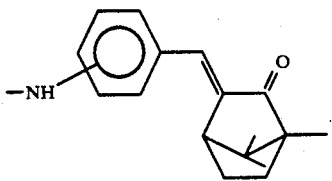 (IV)

which the amino group is in position 2, 3 or 4 with respect to the methylidenecamphor group, provided that:

when $R_2$ is equal to $R_1$, $R_3$ is a radical containing not less than 4 carbon atoms;

when $R_2$ is different from $R_1$ and is of the formula (III), $R_5$ contains not less than 4 carbon atoms when $R_3$ contains 1 to 7 carbon atoms;

when $R_2$ is different from $R_1$ and $R_2$ is not of the formula (III), but is an alkoxy or a mono- or dialkylamino radical, $R_2$ contains not less than 6 carbon atoms when $R_3$ contains 1 to 3 carbon atoms.

2. A Compound according to claim 1, which is selected from the group consisting of: 2,4,6-tris(diisobutyl 4'-aminobenzalmalonate)-s-triazine, 2,4-bis[di(2-ethylhexyl) 4'-aminobenzalmalonate]-6-chloro-s-triazine, 2,4,6-tris[di(2-ethylhexyl) 4'-aminobenzalmalonate]-s-triazine, 2,4-bis[di(2-ethylhexyl) 4'-aminobenzalmalonate]-6-(2-ethylhexyl 4'-aminobenzoate)-s-triazine, 2,4-bis(diisobutyl 4'-aminobenzalmalonate)-6-butoxy-s-triazine, 2,4-bis(diisobutyl-4'-aminobenzalmalonate)-6-(2-ethylhexylamino)-s-triazine, 2,4-bis(diisobutyl 4'-aminobenzalmalonate)-6-(2-ethylhexyl 5'-aminosalicylate)-s-triazine, 2,4-bis(diisobutyl 4'-aminobenzalmalonate)-6-(2-ethylhexyl 4'-aminocinnamate)-s-triazine and 2,4-bis(diisobutyl 4'-aminobenzalmalonate)-6-(4'-aminobenzylidenecamphor)-s-triazine.

3. A cosmetic sunscreening composition for protecting the skin and hair agent ultraviolet radiation which contains an effective sunscreening amount of at least one compound of formula (I) according to claim 1 in a cosmetically acceptable carrier containing at least one fatty phase or one organic solvent.

4. A cosmetic sunscreening composition according to claim 3, which contains at least one compound selected from the group consisting of: 2,4,6-tris(diisobutyl 4'-aminobenzalmalonate)-s-triazine, 2,4-bis[di(2-ethylhexyl) 4'-aminobenzalmalonate]-6-chloro-s-triazine, 2,4-tris[di(2-ethylhexyl) 4'-aminobenzalmalonate]-s-triazine, 2,4-bis[di(2-ethylhexyl) 4'-aminobenzalmalonate]-6-(2-ethylhexyl 4'-aminobenzoate)-s-triazine, 2,4-bis(diisobutyl 4'-aminobenzalmalonate)-6-butoxy-s-triazone, 2,4-bis(diisobutyl 4'-aminobenzalmalonate)-6-(2-ethylhexylamino)-s-triazone, 2,4-bis(diisobutyl 4'-aminobenzalmalonate)-6-(2-ethylhexyl 5'-aminosalicylate)-s-triazone, 2,4-bis(diisobutyl 4'-aminobenzalmalonate)-6-(2-ethylhexyl 4'-aminocinnamate)-s-triazine and 2,4-bis(diisobutyl 4'-aminobenzalmalonate)-6-(4'-aminobenzylidenecamphor)-s-triazine.

5. A cosmetic sunscreening composition according to claim 3 which is provided in the form of an oily or oil-alcohol lotion, emulsion, vesicular dispersion of ionic or nonionic amphiphilic lipids, oil-alcohol or alcoholic gel, solid stick or aerosol.

6. A cosmetic sunscreening composition according to claim 5, which further contains cosmetic adjuvants selected from the group consisting of thickeners, demulcents, humectants, surface-active agents, preservatives, antifoams, perfumes, oils, waxes, lanolin, lower monoalcohols and polyols, propellants, colorants and pigments.

7. A cosmetic sunscreening composition according to claim 3, which is in the form of a human epidermis-protecting composition and contains 0.1 to 2% by weight of a compound of formula (I).

8. A cosmetic sunscreening composition according to claim 3, which is in the form of an antisun composition and contains 0.3 to 15% by weight of a compound of formula (I).

9. A cosmetic sunscreening composition according to claim 8, which further contains an agent screening out UV-B and/or UV-A rays which is different from the compound of formula (I).

10. A cosmetic sunscreening composition according to claim 3, intended to be applied to hair, which is provided in the form of a shampoo, lotion, rinse off gel or emulsion, hair styling or treating lotion or gel, blow drying or hair setting lotion or gel, hair lacquer, permanent wave, bleaching or dyeing composition, and contains 0.1 to 2% by weight of a compound of formula (I).

11. A cosmetic sunscreening composition according to claim 3, in the form of a cosmetic composition stabilised with respect to light, which consists of a hair composition, a make up product or a skin care or treatment composition, containing 0.1 to 2% by weight of a compound of formula (I).

* * * * *